(12) United States Patent
Rosman et al.

(10) Patent No.: US 7,532,375 B2
(45) Date of Patent: May 12, 2009

(54) TUNING-FORK-TYPE SCANNING APPARATUS WITH A COUNTERWEIGHT

(75) Inventors: Gavan Edmund Rosman, Camberwell (AU); Christopher Gerard Byrne, Rowville (AU); Robert Alan Pattie, Nyora (AU)

(73) Assignees: Hoya Corporation, Tokyo (JP); Optiscan Pty Ltd, Notting Hill VIC (AU)

( * ) Notice: Subject to any disclaimer, the term of this patent is extended or adjusted under 35 U.S.C. 154(b) by 272 days.

(21) Appl. No.: 11/575,261

(22) PCT Filed: Sep. 23, 2005

(86) PCT No.: PCT/AU2005/001466

§ 371 (c)(1),
(2), (4) Date: Mar. 14, 2007

(87) PCT Pub. No.: WO2006/032106

PCT Pub. Date: Mar. 30, 2006

(65) Prior Publication Data

US 2007/0242330 A1    Oct. 18, 2007

Related U.S. Application Data

(60) Provisional application No. 60/612,537, filed on Sep. 24, 2004.

(51) Int. Cl.
*G02B 26/08* (2006.01)
(52) U.S. Cl. ........................... 359/196; 359/224
(58) Field of Classification Search ............... 359/196, 359/199, 223–226; 250/306
See application file for complete search history.

(56) References Cited

U.S. PATENT DOCUMENTS

| 4,282,879 | A | 8/1981 | Kunii et al. |
| 5,009,473 | A | 4/1991 | Hunter et al. |
| 5,179,276 | A * | 1/1993 | Hakamata .................. 250/234 |
| 6,294,775 | B1 | 9/2001 | Seibel et al. |
| 7,051,582 | B2 * | 5/2006 | Akiyama .................... 250/306 |
| 2003/0086161 | A1 | 5/2003 | Harris |
| 2005/0052753 | A1 | 3/2005 | Kanai |

FOREIGN PATENT DOCUMENTS

| EP | 1256962 | 11/2002 |
| GB | 2289759 | 11/1995 |
| JP | 58-105213 | 6/1983 |
| JP | 62-226119 | 10/1987 |

(Continued)

OTHER PUBLICATIONS

Derwent Abstract association No. 93-044933/05 (associated with U.S. 5,179,276).

(Continued)

*Primary Examiner*—Euncha P Cherry
(74) *Attorney, Agent, or Firm*—Greenblum & Bernstein, P.L.C.

(57) ABSTRACT

A scanning method and apparatus, the apparatus comprising a fork with first and second forwardly extending tines and a rearwardly extending counterweight member, a mount for supporting the fork at a point between the tines and the counterweight member, and a drive for effecting relative vibration between the tines to provide a fast scan and for driving the fork to provide a slow scan transverse to the fast scan.

23 Claims, 8 Drawing Sheets

FOREIGN PATENT DOCUMENTS

| | | |
|---|---|---|
| JP | 8-334318 | 12/1996 |
| WO | 89/12805 | 12/1989 |
| WO | 99/04301 | 1/1999 |
| WO | 00/75712 | 12/2000 |
| WO | 01/06296 | 1/2001 |

OTHER PUBLICATIONS

Derwent Abstract association No. J1871D/35 (associated with U.S. 4,282,879).

English Language Abstract of JP 8-334318.

Derwent Abstract association No. 2001-122805/13 (associated with WO 00/75712).

Derwent Abstract association No. 97-096305/09 (associated with JP 8-334318).

Derwent Abstract association No. 2001/226410/23 (associated with WO 01/06296).

Derwent Abstract association No. 95-394802/51(associated with GB 2 289 759).

Derwent Abstract association No. 2003-048529/05 (associated with EP 1 256 962).

Derwent Abstract association No. 90-022634/03 (associated with WO 89/12805).

English Language Abstract of JP 62-226119.

English Language Abstract of JP 58-105213.

* cited by examiner

TUNING-FORK-TYPE SCANNING APPARATUS WITH A COUNTERWEIGHT

RELATED APPLICATION

This application is based on and claims the benefit of the filing date of U.S. application Ser. No. 60/612,537 filed 24 Sep. 2004, the content of which is incorporated herein by reference in its entirety.

FIELD OF THE INVENTION

The present invention relates to a scanning apparatus and method, or particular but by no means exclusive application in optical systems including, for example, confocal or multiphoton systems. Such systems may be in the form of, for example, endoscopes, microscopes or endomicroscopes.

BACKGROUND OF THE INVENTION

Optical systems in general and endoscopes in particular may include a scanning system so that a two-dimensional image can be constructed of a sample. In some existing systems, this scanning system provides a raster scan comprising a fast scan (usually described as the x-scan) and a slow scan (usually described as the y-scan).

One existing system is disclosed in WO 99/04301. A scanner is mounted in an optical head casing and light is admitted to the optical head casing by means of an optical fibre mounted on the scanner. In a particular embodiment, the scanner comprises a tuning fork to which the optical fibre is attached. The tuning fork is vibrated, which causes the optical fibre to vibrate thereby providing the fast x-scan. The slow y-scan is provided by moving the tuning fork in a direction perpendicular to the fast x-scan vibration, such as by rotating the tuning fork about its longitudinal axis.

Another existing system, disclosed in U.S. Pat. No. 6,294,775, attempts to integrate the provision of the fast and slow scans, by outputting a beam of light from a resident optical fibre in a spiral or a radial scan path.

However, it is always desirable that still smaller scanning systems be developed, particularly for endoscopic applications. Existing systems each have a lower limit to their practical size, owing to the complexity of their construction, the mechanical properties of their materials or the arrangement of their component. In addition, some existing systems are undesirably complex and therefore are more vulnerable to failure or deterioration of performance.

SUMMARY OF THE INVENTION

In a first aspect, therefore, the present invention provides a scanning apparatus, comprising:
 a fork with first and second forwardly extending tines and a rearwardly extending counterweight member;
 a mount for supporting said fork at a point between said tines and said counterweight member; and
 a drive for effecting relative vibration between said tines to provide a fast scan and for driving said fork to provide a slow scan transverse to said fast scan.

Preferably the fork is mounted substantially at its centre of mass.

Thus, the tines may be driven relative to each other to provide the fast or x scan, while the fork is rocked relative to the mounting point to provide the slow or y scan.

In one embodiment, the drive comprises first and second electromagnetic drives, the first magnetic drive comprising an x-drive coil located about said tines and the second electromagnetic drive comprising a y-drive coil located about said counterweight member, wherein the x-drive coil and the y-drive coil are stationary relative to the mount. In this embodiment, the drive preferably further includes a magnet located on the first tine.

In another embodiment the drive comprises an electromagnetic drive comprising a single drive coil located about said fork.

In one particular embodiment, the apparatus includes a stabilizing magnet located rearward of said counterweight member. This magnet defines the approximate location of the apparatus when not in use, and defines an operational centre when the apparatus is in use. The stabilizing magnet may have a boss or protrusion facing the counterweight member for concentrating the magnetic field lines of the stabilizing magnet in the vicinity of the boss or protrusion.

In a certain embodiment, the mount comprises a deformable material with an aperture in which the fork is located, wherein the deformable material deforms to accommodate motion of the fork. The deformable material may be, for example, rubber, neoprene, silicone, or other artificial polymeric material.

In one particular embodiment, the deformable material is a visco-elastic material, such as sorbothane (a trade mark of Sorbothane, Inc. of Ohio USA) or other polyurethane material.

The apparatus may include a z-axis drive, for driving said fork forwardly and rearwardly. The z-axis drive may comprise a nitinol wire drive.

In one embodiment, the scanning apparatus comprises an optical head of approximately 5 mm diameter and 45 mm length (excluding casing).

In another embodiment, the scanning apparatus comprises an optical head of approximately 3.5 mm diameter and length of at least 100 mm (excluding casing), or 4.4 mm diameter and lengths of up to 300 mm or more including a casing.

The diameter can be reduced if the length of the optical head is increased, because driving coils can be wound more thinly (such as with fewer windings) but—in compensation—greater length to produce comparable field strengths. Similarly, shorter embodiments may be constructed by employing more windings.

Apparatuses with optical head of even smaller diameters can be manufactured (for example, 3 mm diameter) if a reduced tine vibration range and a reduced y deflection range can be tolerated in particular applications. This may reduce the resulting field of view of a scanned image, thereby compromising image gathering functionality, but in some applications the reduction in size may justify the loss of field of view.

In other aspects, the invention provides an optical head comprising the scanning apparatus described above, and an optical instrument (such an endoscope, a microscope or an endomicroscope) comprising the scanning apparatus described above.

In another broad aspect there is provided a scanning method comprising:
 supporting a fork having first and second forwardly extending tines and a rearwardly extending counterweight member at a point between said tines and said counterweight member;
 driving at least one of the first and second tines to vibrate relative to the other of the first and second to provide a fast scan; and
 moving said fork to provide a slow scan transverse to said fast scan.

In one embodiment, the method includes supporting the fork substantially at its centre of mass.

In a particular embodiment, the method includes driving the at least one of the first and second tines by means of a first drive coil located about said tines and moving the fork to provide the slow scan by means of a second drive coil located about the counterweight member, wherein the x-drive coil and the y-drive coil are stationary relative to the point at which the fork is supported.

In another embodiment the drive comprises an electromagnetic drive comprising a single drive coil located about said fork. In this embodiment, the method may include driving the coil with a waveform comprising sequences of positive and negative pulses separated by resting phases, and controlling instantaneous y deflection by controlling the ratio of positive pulses to negative pulses.

BRIEF DESCRIPTION OF THE DRAWINGS

In order that the invention may be more clearly ascertained, embodiments will now be described, by way of example, with reference to the accompanying drawing, in which.

DETAILED DESCRIPTION OF THE EMBODIMENTS

Figure 1:
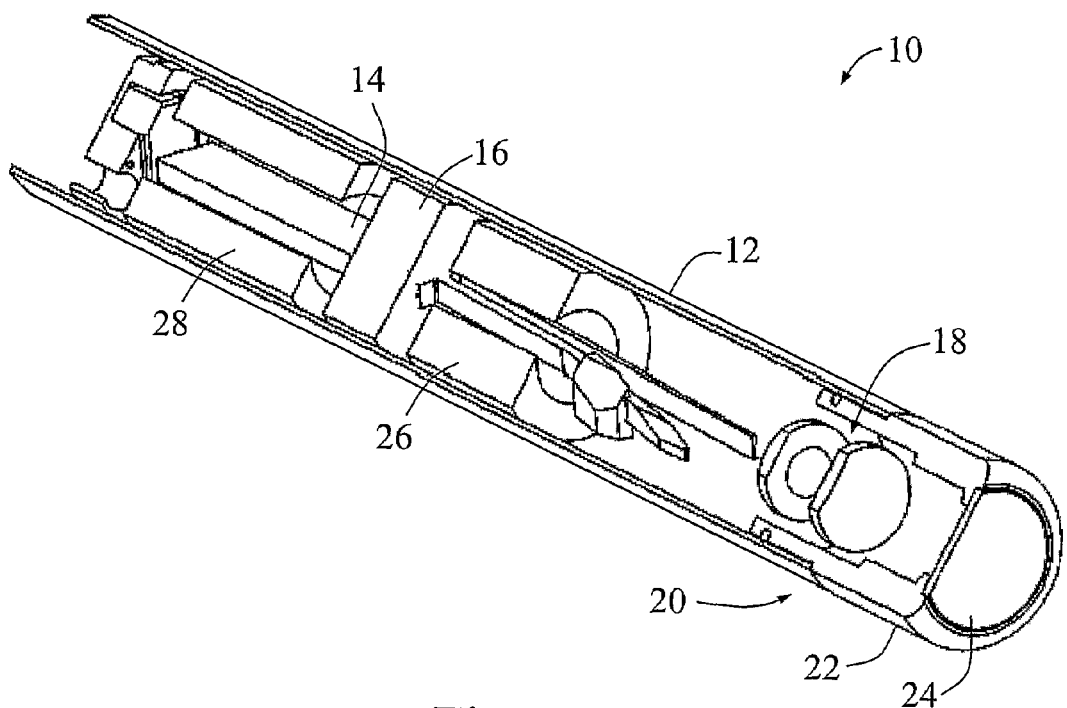
FIG. 1 is a schematic, partial cutaway view of a scanning optical head according to a preferred embodiment of the present invention.

A scanning optical head according to a first embodiment of the invention is shown in partial cut-away view generally at 10 in FIG. 1. The optical head 10 includes a casing 12 containing a fork 14 located in and held by a fork mount 16. The optical head 10 also includes, forward of the fork 14, a lens train 18. The forward end 20 of the casing 12 is closed by means of a cap 22 that includes a forwardly facing window or cover glass 24.

The optical head 10 has been constructed with an external diameter of less than but approximately equal to 5 mm (excluding casing 12) and a length of less than but approximately equal to 45 mm. However, another embodiment has been constructed with a diameter of approximately 3.5 mm (excluding casing 12) or 4.4 mm including the casing 12; in this embodiment the optical head 10 excluding casing has a length of at least 100 mm, with lengths of up to 300 mm when the casing is included and depending on application.

The fork 14, in use, supports and scans an optical fibre (not shown); light exiting the optical fibre in a forward direction can therefore be scanned over a sample, while light returning from that sample can be received by the optical fibre confocally and transmitted to a photodetector or other instrumentation.

In order to drive the fork 14, optical head 10 includes a drive including an x-drive and a y-drive. In this embodiment, the x-drive is in the form of an x-drive coil 26, which is located forward of fork mount 16; the y-drive is in the form of a y-drive coil 28 located rearward of fork mount 16. (The x-drive and the y-drive also include associated electronics that are located outside and remote from the optical head; these are discussed below by reference to FIGS. 7 and 8.) The x-drive coil 26 encircles the tines of fork 14 over approximately half their length at their rearward end (i.e. adjacent to the fork mount 16). The y-drive coil 28 encircles most of the length of the fork 14 that is rearward of the fork mount 16.

In use, less massive tine 30 can be vibrated with an amplitude of ±1.4 mm at its tip. The fork 14 can be rocked in the y direction (i.e.) such that the tines 30, 32 are moved perpendicular to their direction of vibration with an amplitude of ±1 mm (i.e. a total travel of 2 mm) from the axial, at rest orientation; this equates to y deflection angle for fork 14 of ±3.45°.

Figure 2:
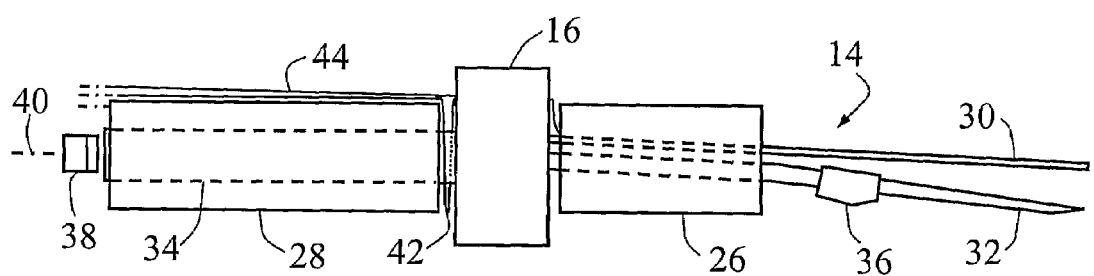
FIG. 2 is a schematic plan view of the fork, fork mount and scanning coils of the optical head of FIG. 1.

FIG. 2 is a schematic representation of the fork 14, fork mount 16, x-drive coil 26 and y-drive coil 28 in plan view. The fork 14 is cut from a 0.65 mm thick sheet of silicon steel and includes forwardly extending first and second tines 30, 32 and a rearwardly extending counterweight member 34. The fork 14 is mounted at its centre of mass within fork mount 16, which comprises a cylindrical block of sorbothane with a slot (not shown) sized to fit the fork 14. The fork 14 is either held in place owing to the resilient nature of sorbothane, or can additionally be held in the fork mount 16 with glue.

In use, an optical fibre is located on tine 30; a hole of suitable size is provided in fork mount 16 so that this optical fibre can pass through the mount and thereby conduct light from a light source external to the optical head 10 via the rearward end of optical head 10 to the forward end of tine 30. Tines 30, 32 acts as mutual counterbalances, but tine 32 is more massive so that, in use, tine 32 has a lesser amplitude than less massive tine 30. This allows tine 30 to have a greater amplitude without striking the more massive tine 32, thereby providing a scan of increased range.

The fork 14 is of a magnetically permeable material so that it can be driven by the x-drive coil 26 and the y-drive coil 28. Furthermore, the x-drive additionally comprises a permanent biasing magnet 36 mounted on more massive tine 32 so that greater driving force for driving the tines 30, 32 can be generated, owing to the interaction of the magnetic field generated by x-drive coil 26 and biasing magnet 36. As will be discussed in greater detail below, biasing magnet 36 is adjustably mounted on more massive tine 32 so that its position on more massive tine 32 can be adjusted so as to alter the vibrational characteristics of fork 14. This allows the tines 30, 32 to be tuned to a preferred frequency; hence, the fork 14—once provided with biasing magnet 36—may be described as tunable. The resonance frequency of the x scan is set to be between 800 to 850 Hz, and this can be fine tuned by adjusting the position of the biasing magnet 36 before it is glued into its final position. The y scan is operated at approximately 80 Hz.

The optical head 10 also includes a stabilizing permanent magnet 38, located rearward of counterweight member 34. This stabilizing magnet 38 forms a part of the y-drive (as is discussed below by reference to FIG. 6). In addition, however, stabilizing magnet 38 serves to attract counterweight member 34; hence, stabilizing magnet 38 tends to define an operational centre when the optical head 10 is in use, and holds the fork 14 with a fork angle θ of approximately zero (i.e. approximately parallel to the longitudinal axis 40 of optical head 10) when the optical head 10 is not in use. This latter effect has the benefit of reducing the tendency of fork 14 to sag under its own weight within fork mount 16; such sag could otherwise progressively deform the sorbothane constituting mount 16.

Also depicted in FIG. 2 are a cable bundle 42 and optical fibre 44. The cable bundle 42 includes a pair of power cables for the x-drive coil 26, and cables for an x position sensor (viz. sensor 106 of FIG. 9A: see below). The cables and optical fibre are admitted to the optical head 10 at its rearward end. The cable bundle 42 are wound in one complete loop around the interior of the casing 12 in that portion of the optical head 10 between the mount 16 and the y-drive coil 28, before being accommodated in the mount 16 and admitted to that portion of the optical head 10 forward of the mount 16. This is to isolate the mount 16 and fork 14 from any expansion or contraction of the cables due to variations in operating temperatures, lest the alignment of the fork be affected. The optical fibre 44 does not include such a loop.

After being admitted to the forward portion of the optical head 10, the cables are connected to the x-drive coil 26 and x position sensor (not shown) respectively, and optical fibre is accommodated in a groove (not shown, but see FIG. 3) in the outer surface of less massive tine 30.

Figure 3:
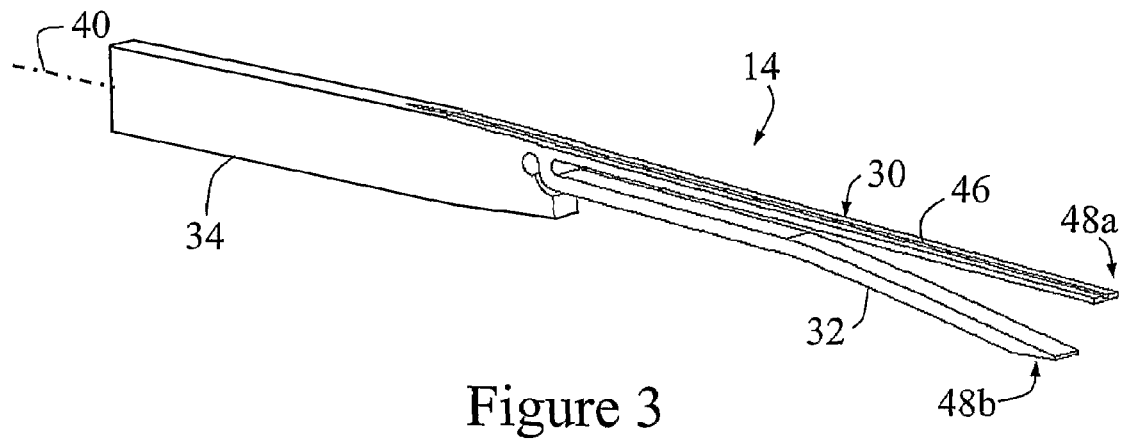
FIG. 3 is a perspective view of the fork of FIG. 1.

FIG. 3 is a perspective view of fork 14. As is apparent from this view, the less massive tine 30 has a groove 46 in its outer surface; this groove 46 is for accommodating an optical fibre, which is glued into the groove with the fibre's tip essentially coincident with the forward end 48a of less massive tine 30. More massive tine 32, in the equilibrium position depicted in FIG. 3, tends downwardly relative to the longitudinal axis of fork 14 so that, as discussed above, less massive tine 30 can vibrate with the greatest possible amplitude without interfering with more massive tine 32. Further, the forward end 48b of more massive tine 32 is pointed to maximize the envelope of its motion that can be accommodated within casing 12.

Figure 4:
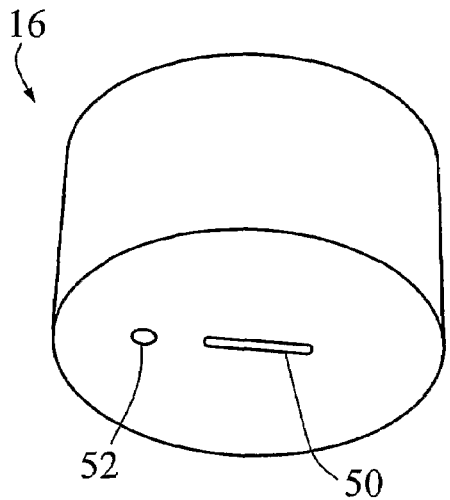
FIG. 4 is a perspective view of the fork mount of the optical head of FIG. 1.

FIG. 4 is a view of fork mount 16. The mount 16 has a slot 50 for receiving and retaining the fork 14. As noted above, the mount 16 comprises a cylindrical bock of sorbothane; sorbothane is selected for its flexibility, which allows fork 14 to describe the desired y scan, and for its resilience, which assists in retaining fork 14 (supplemented if desired by glue) in slot 50 and in urging fork 14 back to an equilibrium position after deflection in the y direction. The mount 16 also has an aperture 52 for accommodating optical fibre 44 (for mounting on less massive tine 30) and the cable bundle 42 (comprising the power cables for the x-drive coil 26, and cables for an x position sensor).

When the casing 12 is metal, one of the pair of power cables for the x-drive coil 26 can be earthed to the casing 12, so need not be accommodated by aperture 52.

In other embodiments these cables 42 and the optical fibre 44 could alternatively be accommodated by a plurality of such apertures in the mount 16, or sited alongside the fork at the mount and admitted through slot 50 (in which case the slot could be modified in shape as required).

Figure 5:
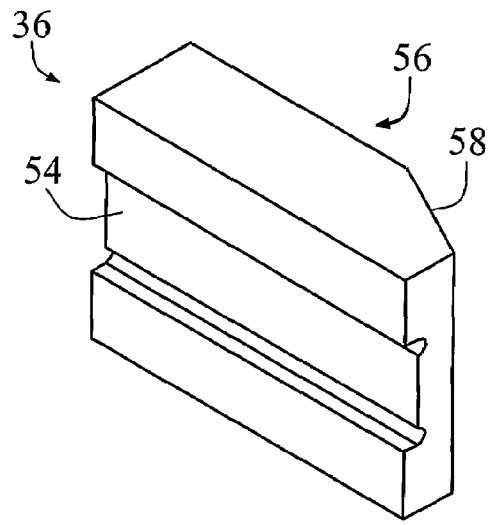
FIG. 5 is a perspective view of the permanent (or x) magnet of the optical head of FIG. 1.

FIG. 5 is a view of biasing magnet 36. This magnet is designed so that its position, once mounted on more massive tine 32, can be adjusted until as desired, then glued in place. The biasing magnet 36 thus includes a groove 54 for receiving the more massive tine 32. The groove 54 is sized so that the biasing magnet 36—when pressed onto the more massive tine 32—will remain in place temporarily until its position is adjusted as desired and glue is applied to more permanently secure biasing magnet 36.

The side 56 of the biasing magnet 36 that—in use—faces the casing 12 is provided with a taper 58; the biasing magnet 36 is mounted on the more massive tine 32 oriented with this taper 58 closer to the forward end 48b of more massive tine 32, to reduce any interference by biasing magnet 36 with the casing 12.

Figure 6:
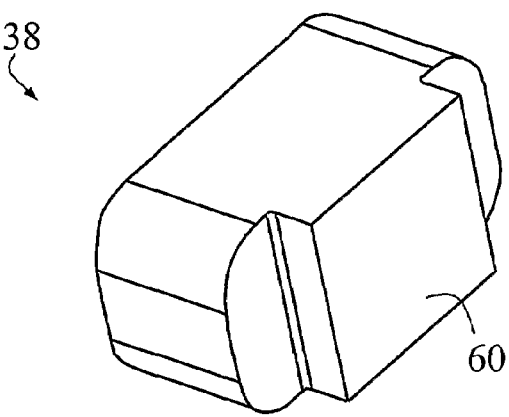
FIG. 6 is a perspective view of the stabilizing (or y) magnet of the optical head of FIG. 1.

FIG. 6 is a view of stabilizing permanent magnet 38. Stabilizing magnet 38 has a boss 60 that, when stabilizing magnet 38 is located within the casing 12 of optical head 10, faces forward towards the counterweight member 34 of fork 14. The stabilizing magnet 38 is given this shape in order to concentrate its magnetic field lines in the vicinity of the boss 60. As discussed above, this provides a high stabilizing force when the fork is oriented within the casing 12 with a fork angle θ=0 (i.e. parallel to the longitudinal axis 40 of optical head 10), but a lesser force when—in use—the fork is otherwise oriented.

Stabilizing magnet 38 also forms a part of the y-drive. The y-drive coil 28 is driven by a current with essentially a sawtooth waveform (see FIGS. 10 and 11). When current is passed through the y-drive coil 28 a magnetic pole is induced in the rearward end of counterweight member 34. Starting with the fork 14 in its stabilized resting position and oriented axially, as a DC current (supplied by current source 132 of FIG. 8) is added to y-drive coil 28 a magnetic pole (north or south depending on the direction of the current) at the rearward end of the counterweight member 34 of fork 14. Owing to the proximity of the stabilizing magnet 38, the stabilizing magnet's magnetic field and that induced in fork 14 interact and prompting relative movement between the rearward end of the fork 14 and the stabilizing magnet 38. Thus, in use, the DC current is increased from zero to a maximum value $I_{max}$, at which point the fork 14 reaches the maximum desired y deflection. The DC is then reversed to $-I_{max}$ causing the orientation of the magnetic pole induced in the rearward end of counterweight member 34 to reverse (viz. from north to south or vice versa); this causes the fork 14 to be urged to the maximum y deflection in the opposite direction. This reversal constitutes a fly back in the y. The DC current is then ramped from $-I_{max}$ to zero and from there to $I_{max}$ as the process is repeated. The y scan component of the raster scan is thus effected.

The angle of deflection of the fork 14 as a function of the magnetic field strength (and hence of drive current) of the y-drive coil has been found to be acceptably linear over the ±3.45° y deflection range mentioned above. In addition, non-linearities in the y-drive arising from other factors can be reduced when the apparatus is in operation: this is discussed by reference to FIGS. 10 and 11 below.

Figure 7A:
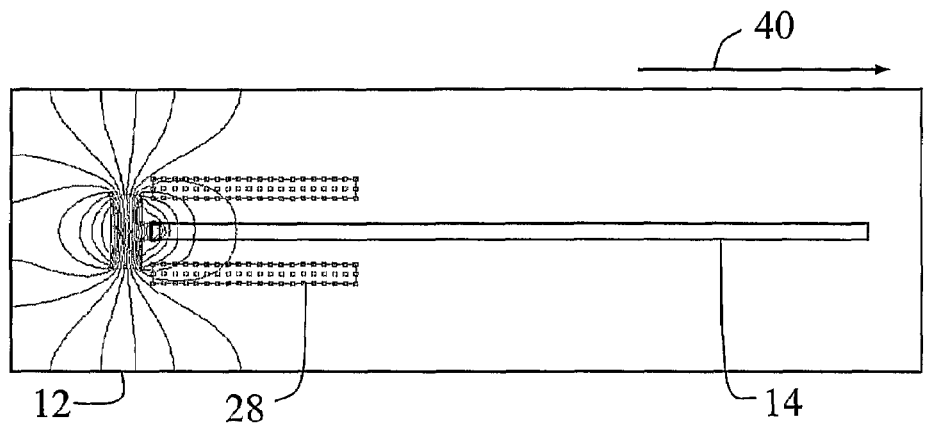
FIGS. 7A and 7B are schematic views of the magnetic field of the stabilizing (or y) magnet of the optical head of FIG. 1, in relation to the fork and y-drive coils of the optical head of FIG. 1.
Figure 7B:
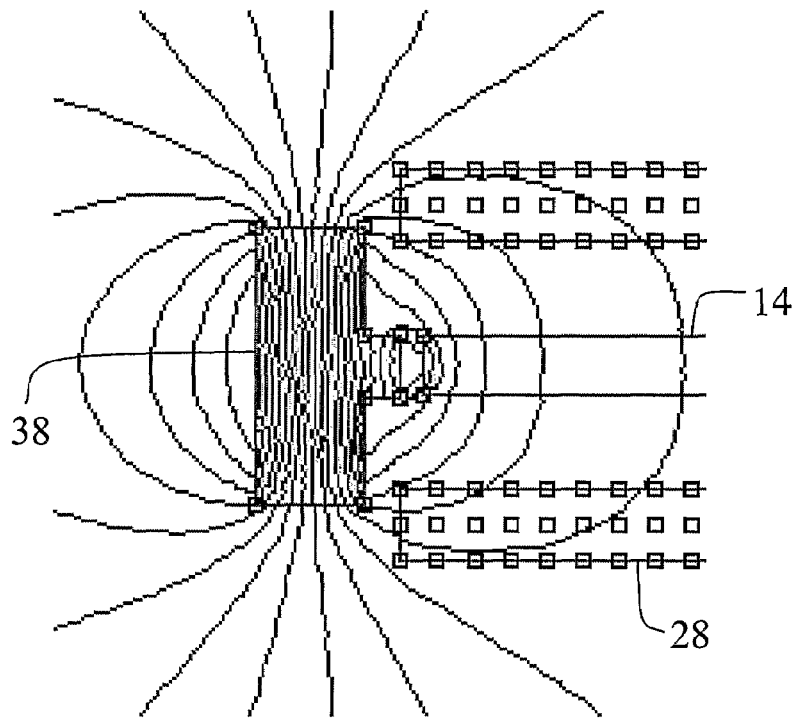

FIG. 7A is a diagram of the casing 12, fork 14, y-drive coil 28, stabilizing magnet 38 and magnetic field lines produced by the stabilizing magnet 38. FIG. 7B is a detail of FIG. 7A, more clearly showing the field lines and the way in which they are concentrated around the boss 60 and hence near the rest or axial location of the rearward end of fork 14. It will be noted that the field of the stabilizing magnet 38 has, in a sense, two components: an "inner" field created by the boss 60 (whose effect is essentially limited, owing to its shape, to the stabilizing magnet 38) and an "outer" field generated by the whole magnet.

Figure 7C:
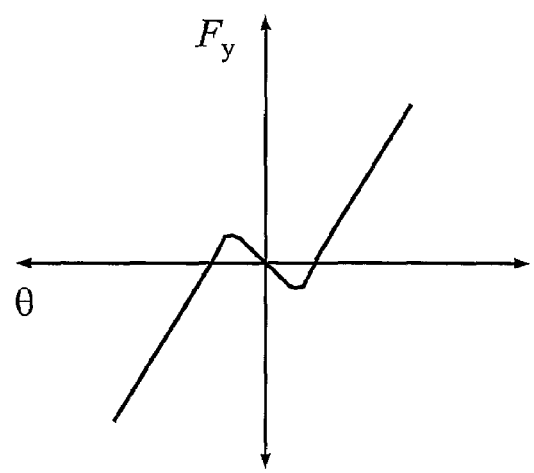
FIG. 7C is a schematic plot of force in the y direction versus fork angle produced by the arrangement of FIGS. 7A and 7B.

FIG. 7C is a schematic plot of the force in the y direction ($F_y$) versus fork angle ($\theta$) relative to the longitudinal axis of the optical head 10, for the arrangement of FIGS. 7A and 7B. $F_y$ is a composite force arising from the stabilizing magnet 38 and the resilience of the mount 16. It will be noted that a localized negative slope in the curve occurs around the origin: this is due to the provision of boss 60 on stabilizing magnet 38.

A number of possible waveforms of the driving current in the x-drive coil 26 are depicted in FIGS. 8A, 8B, 8C and 8D at 80, 82, 84 and 86 respectively. Waveforms 80 and 82 are square waves with pulses of equal magnitude A, though positive in the case of waveform 80 and negative in the case of waveform 82. The pulses in both cases are separated by a resting phase of width equal to the width of the pulses.

Waveform 84 has pulses identical with those of waveforms 80 and 82, but alternating between positive and negative and separated by a resting phase. Waveforms 80, 82 and 84—having resting phases—can be used without a biasing magnet 36.

Waveform 86, however, does not have a resting phase and is used with biasing magnet 36. It also has a small positive DC component; approximately 55% of the peak-to-peak amplitude A is positive, and approximately 45% negative. As it does not include a resting phase, waveform 86 does not rely exclusively on repulsive forces between the tines 30, 32; rather, one repulsive phase is provided, followed immediately (i.e. without a resting or neutral pole waveform) by an attractive phase in which charge is stripped from the two tines and the biasing magnet provides attraction between the tines 30, 32.

Figure 9A:
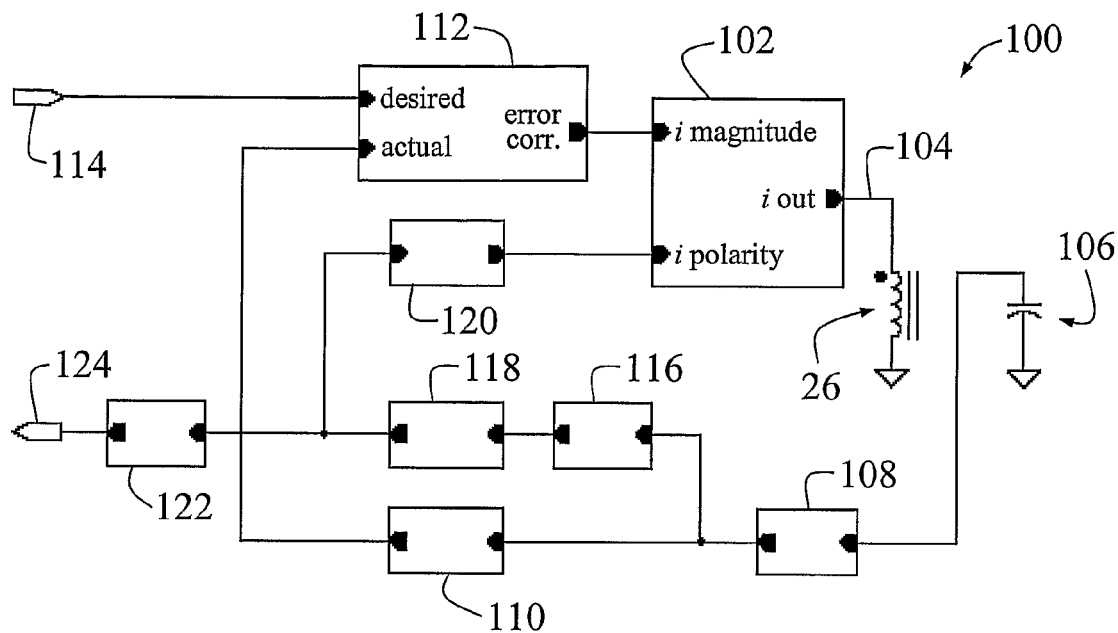
FIG. 9A is a circuit diagram of the x drive of the optical head of FIG. 1.

FIG. 9A is a schematic diagram of the x-drive circuit 100 for the x-drive coil of the optical head of FIG. 1. The fork x-drive coil 26 is driven with an alternating current, the transitions of which are timed to coincide with peak deflection or relaxation of the tines 30, 32. A current drive is employed rather than a voltage drive because a current drive makes the drive independent of the length of cable going to the x-drive coil 26, which may otherwise change the field of view in the x plane if the connecting cables were changed.

This is provided by means of a current source 102 that has a precise voltage to current translation circuit; the output 104 of this current source is fed to the x-drive coil 26. The direction or polarity of the current can be selected to be positive or negative as required by the deflection or relaxation, and the magnitude of the current can be set to that required to achieve the desired deflection or relaxation range, or field of view (FOV) in the x plane.

A number of factors can affect the actual deflection or relaxation, so an x position sensor 106 is mounted on more massive tine 32 at a location within the x-drive coil 26. The x position sensor 106 comprises piezo flexor sensor that outputs a signal that is a function of the flexing of the sensor; that flexing is caused by the flexing of the tine 32, so the sensor's output signal provides a direct measure of the deflection of the tine 32. Tine 32 moves about 20% of the movement of the less massive tine 30, so the output signal from the sensor 1067 provides a measure of the position of the less massive tine 30 and hence of the tip of an optical fibre glued into the groove 46 of less massive tine 30.

The initial value of the output signal of sensor 106 corresponds to the rest position of the more massive tine 32; as the more massive tine vibrates, the output signal varies accordingly and thus allows closed loop operation. The sensor 106 comprises a piezo film, as this type of sensor requires minimal energy to produce an usable output, does not alter the mechanics of the scanning system appreciably, and has good linearity.

The output of the x position sensor 106 is fed into a narrow band pass filter 108 with pass frequency centred around the centre frequency of the fork 14. The narrow band pass filter 108 is placed in the signal line in this manner to remove electrical perturbations of the signal prior to an amplitude detector 110, principally to remove 50/60 Hz noise. The narrow band pass filter 108 thus ameliorates the effect of locating the x position sensor 106 remote from the electronics. A high pass filter could alternatively be employed for this purpose, but a band pass filter has the added advantage that phase delay is zero at the centre frequency.

The output of this filter 108 is input into the amplitude detector 110, which converts the A/C filtered output of the band pass filter 106 into a D/C voltage that accurately reflects the degree of mechanical peak deflection of the tines 30, 32 at any time.

The output of the amplitude detector 110 is the input into a computational circuit 112 (which may be analogue or digital) that implements a PID algorithm. The computational circuit 112 has a number of programmable parameters, most notably the levels of proportional, integral and differential gain used to determine the optimal level of correction, and filters the signal to prevent the control loop from responding to sudden changes outside the dynamic range of the system.

It is desirable to have the deflection or relaxation amplitude in the x plane maintained at a constant but selectable level, so a set input—referred to herein as the horizontal or x-span 114—is applied to the "desired" input of computational circuit 112.

The output of the band pass filter 108 is also applied to the input of a delay circuit 116; delay circuit 116 delays the input to a zero-crossing detector 118 by a small amount so that the zero-crossing detector 118 is not affected by electrical noise in the PCB traces. Such noise in the traces occurs as the current source switches from one state or polarity to the other. The delay thus introduced is only small in comparison to the delay that would have occurred had a high pass filter been used instead of band filter 108. A high pass filter would thus necessitate a separate delay.

The output of the delay circuit 116 is thus applied to the zero-crossing detector 118 to recover precise phase information for synchronizing the separately acquired image information to the instantaneous position of the tines 30, 32. The instantaneous position of the tines provides a measure of the position of the tip of the optical fibre mounted on the less massive tine 30.

The output of the zero-crossing detector 118 is applied to the input of a phase control circuit 120, which allows the transition of the current drive to be timed so that such that it coincides with the peak deflection and relaxation of the tines 30, 32 of the fork 14.

The output of the zero-crossing detector 118 is also applied to a level shifting circuit/image synchronization circuit 122 that reduces the introduction of phase noise into the x-sync signal 124; the x-sync signal 124 is used in the synchronization of the separately acquired image data stream. The x-sync signal 124 is also applied to the y-scan or vertical plane circuitry so that the two are lock stepped to provide a stable image: this is discussed below.

Figure 9B:
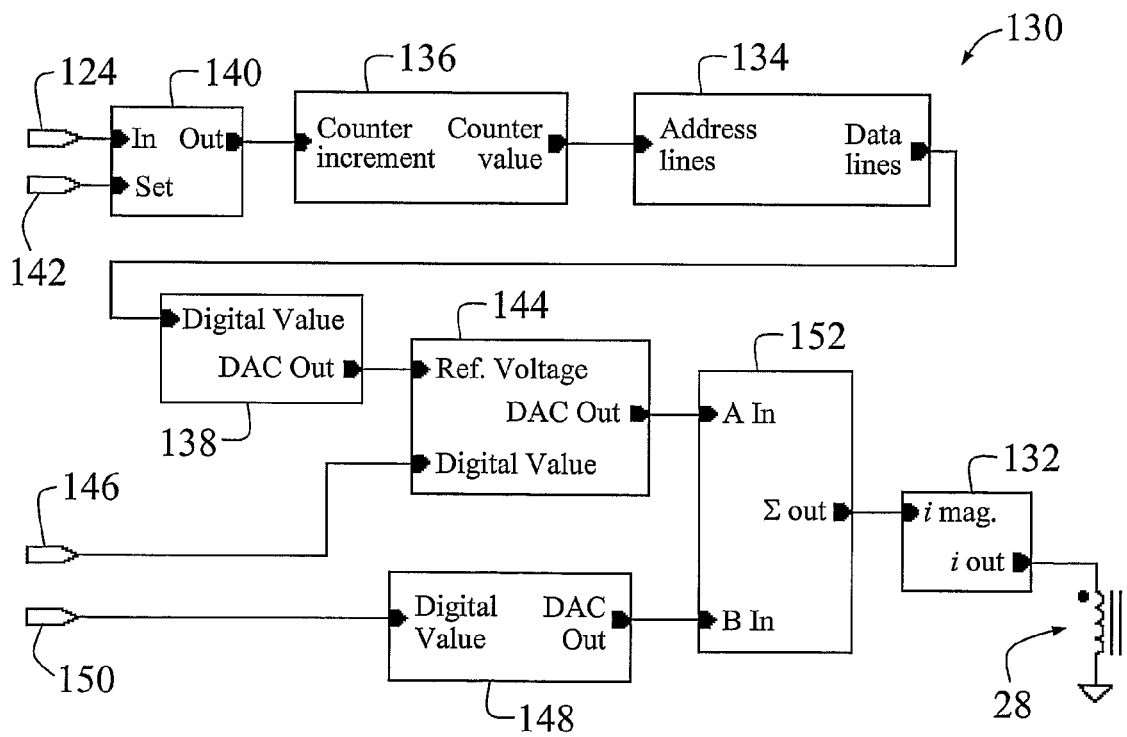
FIG. 9B is a circuit diagram of the y drive of the optical head of FIG. 1.

FIG. 9B is a schematic diagram of the y-drive circuit 130 for the y-drive coil of the optical head of FIG. 1.

The y-drive coil 28 is driven with a current rather than a voltage as this makes the deflection largely independent of the cabling and connection losses. The waveform has a shape in the time domain that ensures the movement of the fork tip in space approximates a linear path in the space domain. This is effected by use of a linear current source 132, the output of which applied to the y-drive coil 28.

Linear current source 132 provides a linear voltage to current conversion. While the electrical components of the drive afford good linearity, there are non-linearities in the mechanical and magnetic aspects of the drive, so the drive current is shaped to achieve linear or substantially linear deflection. This in principle could be done by means of a feedback signal from a sensor that measures the tine displacement, but size limitations and the fact that non-linearities are commonly functions of time and temperature suggest that acceptable shaping of the drive waveform can in many applications provide similar results.

To provide flexibility, the drive circuit 130 uses a wave table stored in a rewriteable memory 134 so that essentially any desired wave form can be recreated. The rewriteable memory 134 may be loaded at any time to accommodate different scan requirements. To get the wave table to drive the fork Y-coil a number of supporting systems are used.

Firstly the address lines of the rewriteable memory 134 are connected to a counter 136 that can be incremented one count at a time. This causes the data in sequential address locations of the rewriteable memory 134 to be output on its data lines. The data lines are applied to the data inputs of a digital-to-analogue-converter, referred to herein as the "Wave DAC" 138. This configuration produces a series of analogue voltages each of which is the result of the value written to the input of the Wave DAC 138.

Additional control of the repetition rate of one complete cycle of the stored pattern is provided by means of a programmable divider 140 which, for the sake of simplicity, can be set to $2^n$ ratios by setting a scan rate input 142. This allows the ready changing of the scanning rate in powers of 2.

The output of the Wave DAC 138 is applied to the reference input of a second DAC, referred to as "Span DAC" 144; the gain/loss of the waveform produced by the Wave DAC 138 can in effect be set by applying a different digital value to the data lines of this Span DAC 144 by means of a set vertical span input 146.

The y-drive circuit 130 includes an Offset DAC 148, which has a set vertical offset input 150. The outputs of the Span DAC 142 and the Offset DAC 148 are input into a summing circuit 152, which produces an output voltage that is then converted to a current by the aforementioned current source 132.

The waveform output by the current source 132 is thus definable in terms of shape, amplitude and offset.

To lock this y plane (or slow) scanning system to be intrinsically locked to the x plane (or fast) scanning system, the x-sync signal 124 from the x-drive circuit 100 provides the increment or "next wave value" selection signal used by the divider circuit 140. Together the two circuits 100 and 130 provide a precise mechanism for controlling the fork 14 to scan in a raster pattern for imaging purposes.

As discussed above, a sawtooth-like current waveform is applied to the y-drive coil (in the two coil embodiment shown in FIG. 1). However, although this waveform may be used initially, the waveform is then adjusted in order to linearize the resulting scan as much as possible. This is done by performing a test scan of a regular grid, then analyzing the resulting image to assess the linearity of the grid image. The waveform is then modified iteratively until the optimum available linearization for a particular device is obtained. Linearization may also change the aforementioned operational centre to some extent.

Figure 10:
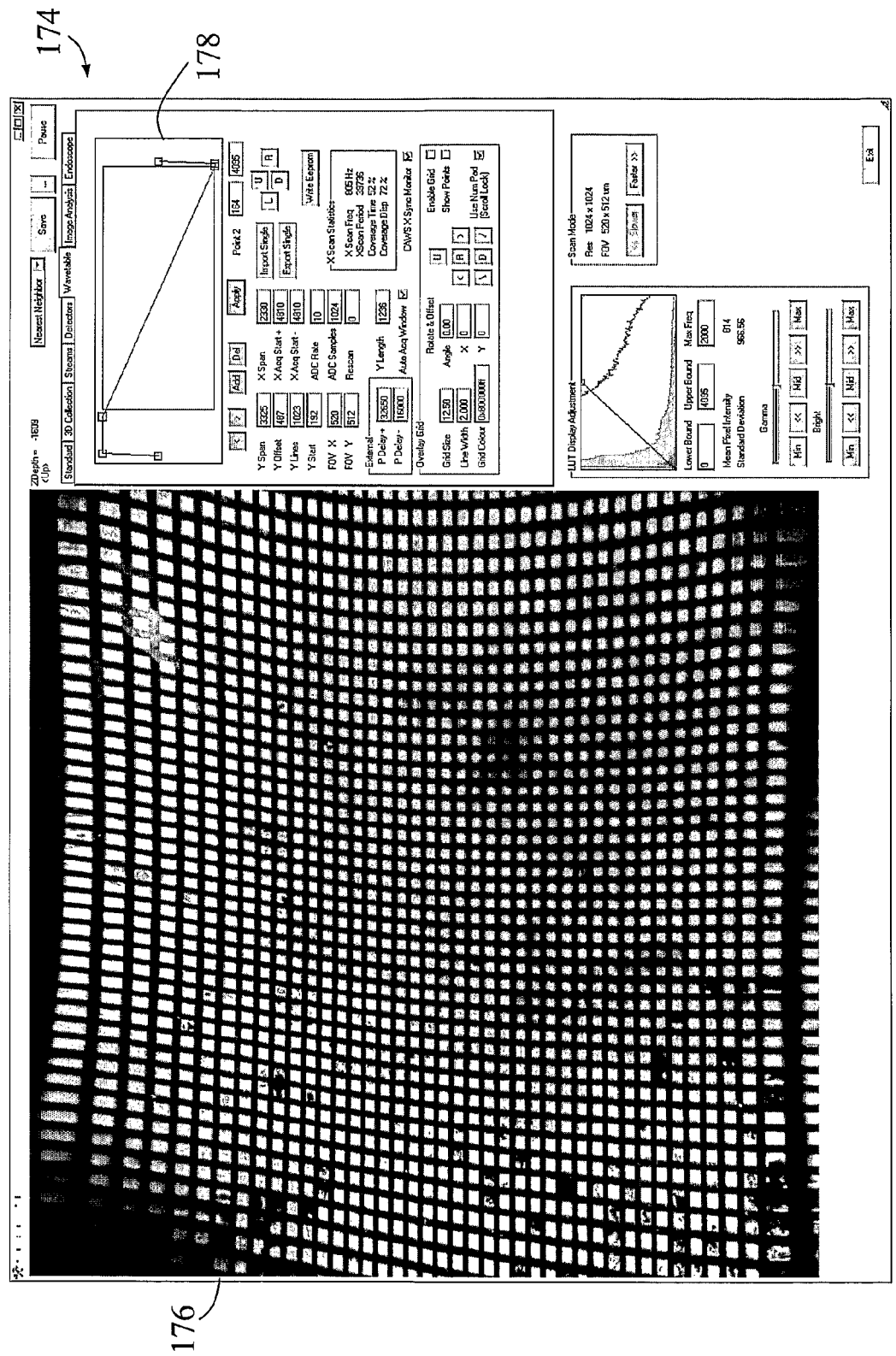
FIG. 10 is a photograph of a grid obtained by means of the optical head of FIG. 1 before scan linearization.

FIG. 10 is a screen-grab of the software control panel 174 of a system for testing and controlling optical head 10, including the image 176 of a regular test grid and a wavetable 178 of the waveform used to drive the y-drive coil 28. As is apparent from wavetable 178, the y-drive waveform is essentially a sawtooth. This causes y-drive coil 28, through its interaction of its magnetic field with the field of the stabilizing magnet 38, to drive the fork to execute a slow scan from a first extreme deflection in the y direction to the other extreme, then rapidly returns the fork to the first extreme deflection in the y direction, after which the sequence is repeated.

Figure 11:
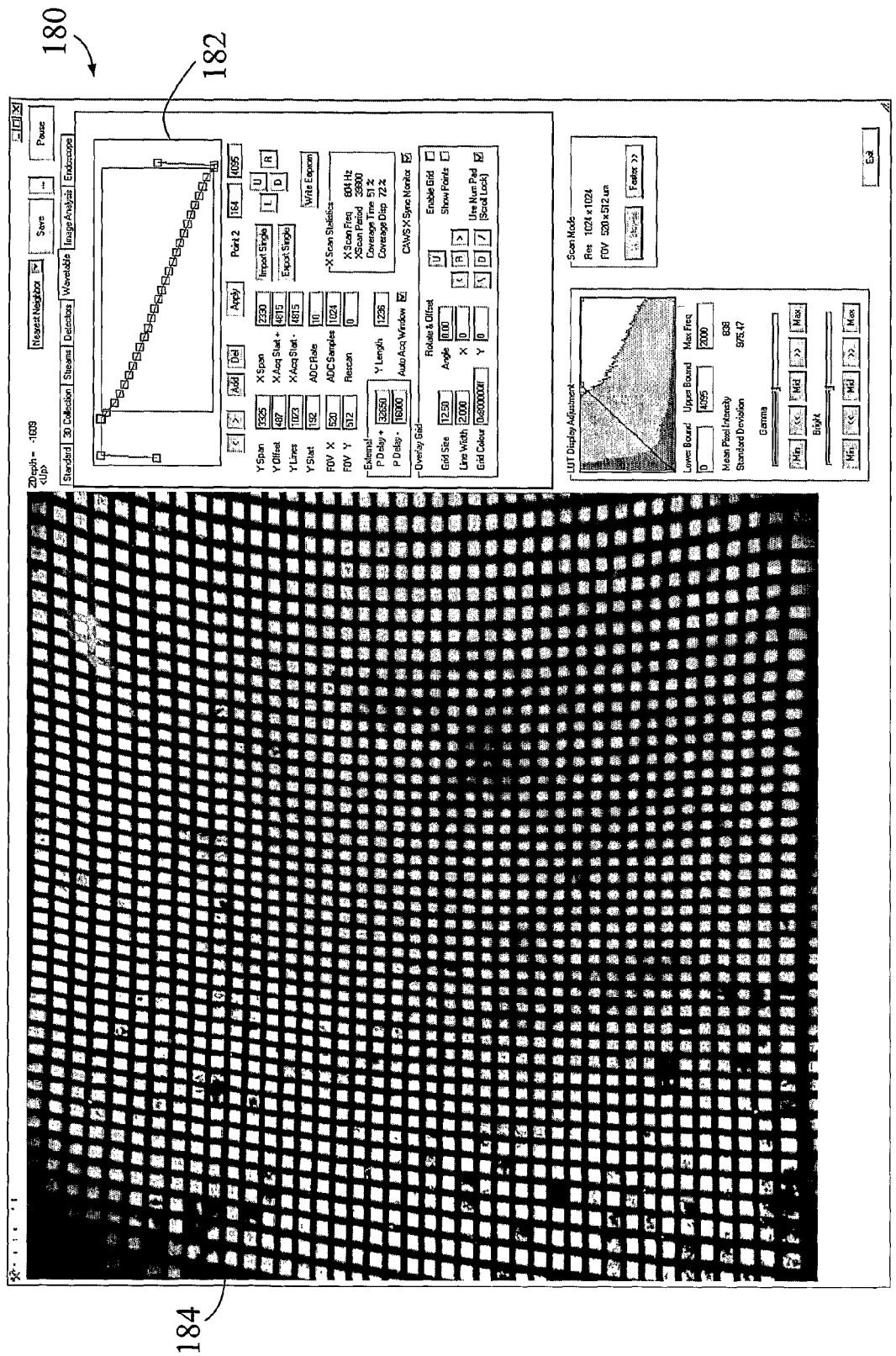
FIG. 11 is a photograph of a grid obtained by means of the optical head of FIG. 1 after scan linearization.

Image 176 was collected before linearization was performed, so the wavetable 178 is linear. FIG. 11 is a comparable screen-grab of the software control panel 180 after linearization has been performed. Owing to adjustments to the waveform, the wavetable 182—though still essentially sawtooth-like—is no longer linear, but the image 184 of the test grid has improved linearity. This is particularly evident when the top and bottom portions of the two images 176, 184 are compared.

The need to modify the waveform arises from the varying forces applied to the fork 14 when at upper maximum y deflection compared with when at the mid-point y deflection and the lower maximum y deflection. This depends on:

the proximity of the fork 14 to the x-drive coil 26;
the effect of the varying current in the y-drive coil being transferred along the length of the fork 14;
the variable elastic resistance exerted by the sorbothane mount 16 as a function of fork travel in the y direction.

The optical head 10 may optionally include a z-drive of any suitable type, such as that provided by means of nitinol wire and Bowden cable and described in U.S. Pat. Ser. No. 10/822, 718 filed 13 Apr. 2004 (whose content is incorporated herein by reference), published 4 Nov. 2004 under publication no. US 2004/0220453.

Figure 12:
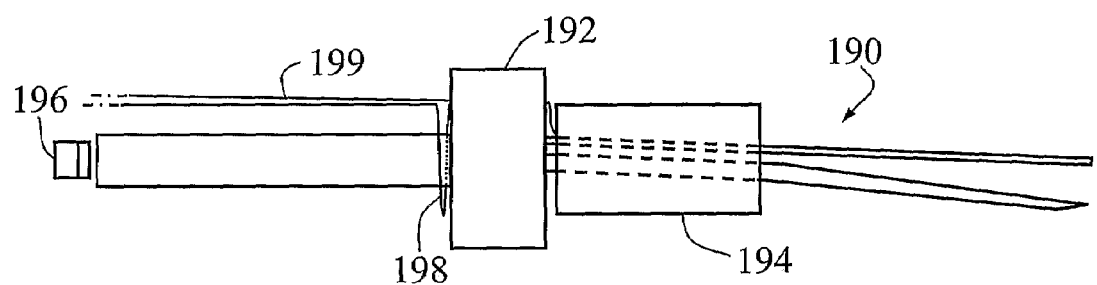
FIG. 12 is a schematic plan view of a fork, fork mount, scanning coil and stabilizing magnet of an optical head according to a second preferred embodiment of the invention.

A fork 190, fork mount 192, drive coil 194 and stabilizing magnet 196 according to a second embodiment of the invention are shown schematically in FIG. 12. These components are suitable for use in an optical head comparable to that of FIG. 1 but, unlike the optical head 10 of FIG. 1, this embodiment has only a single drive coil. A separate y-drive coil is omitted, and drive coil 194 performs the functions of both an x-drive coil and a y-drive coil. This embodiment does not include a biasing magnet (cf. biasing magnet 36). In other respects, however, fork 190, fork mount 192, drive coil 194, cable bundle 198 and optical fibre 199 are identical with fork 14, fork mount 16, x-drive coil 26, cable bundle 42 and optical fibre 44 of the embodiment of FIG. 1.

It is envisaged that, although it may be more difficult to obtain a linearity comparable to that of the two coil embodiment, the single coil embodiment will permit the construction of a more compact optical head.

Figure 8A:
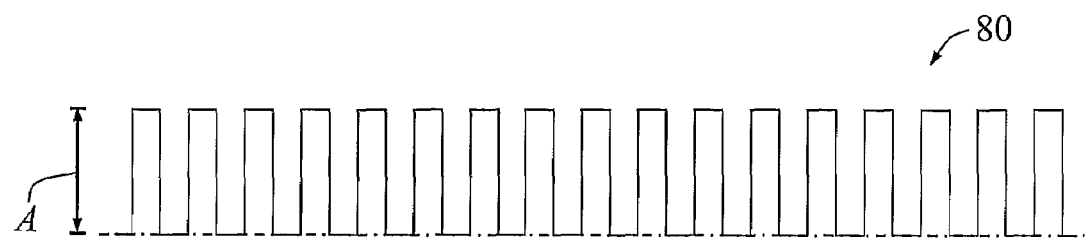
FIGS. 8A, 8B, 8C and 8D are plots of alternative drive signal waveforms for use with the embodiment of FIG. 1.
Figure 8B:
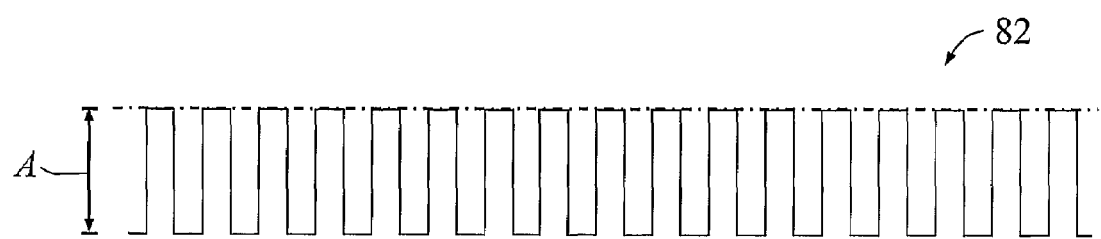
Figure 8C:
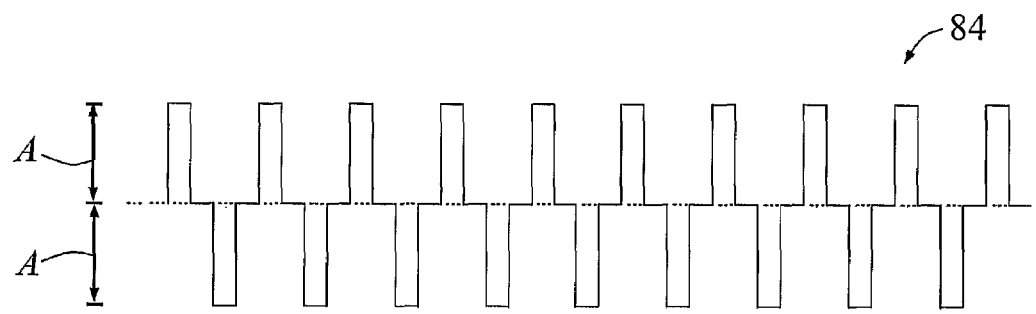
Figure 8D:
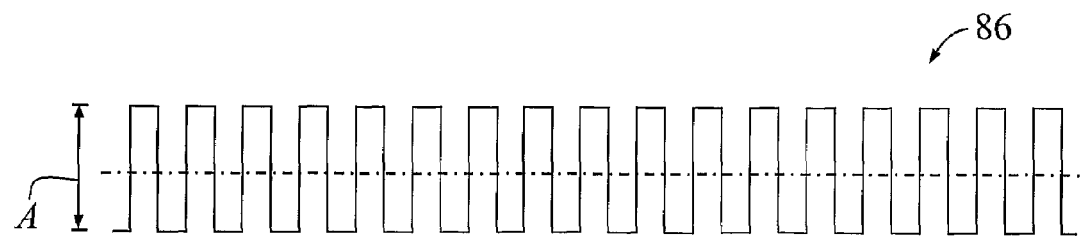

The waveform of the driving current in the drive coil 194 is developed from waveform 84 of FIG. 8C; waveform 84 is essentially square but with a resting phase between positive and negative pulses. The positive pulses, negative pulses and resting phases all have the same duration. The basic waveform does not have a DC component. Consequently, the average of waveform 84 is zero.

However, this average value can be used to produce a y scan, as the average magnetic field rocks the fork 190. The x scan is not affected as long as the pulses recur at the right time.

Also, the x feedback needs no changes, as it is insensitive to coil polarity. (That is, the tines 30, 32 will always mutually repel if there is current in the drive coil 194, so will only return if there is a finite relaxation time between positive and negative pulses. At resonance the tines move from closest to furthest apart as maximum work is done by the magnetic force.)

Hence, waveform 84 will not produce a y scan but, by introducing a positive or a negative DC offset, the fork 190 can be driven in a positive or negative y position. If this offset is, for example, equal to pulse amplitude A of waveform 84, the fork is driven to respective extremes of its y deflection range. Intermediate values of y deflection are then obtained with lesser DC offsets.

Figure 13:
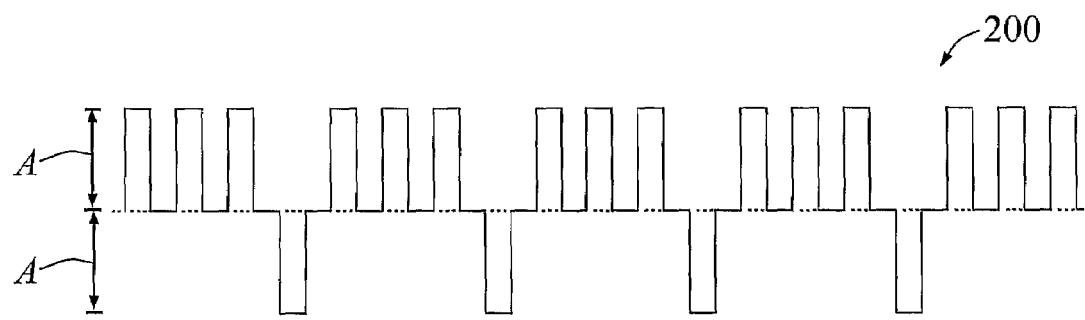
FIG. 13 is a schematic plot of the drive signal waveform for use with the embodiment of FIG. 12.

However, intermediate values of y deflection can also be obtained without employing a DC offset by using waveform 84 but making a fraction of the pulses negative. The average of the waveform, and whether it is positive or negative, is determined by the ratio of positive and negative pulses. If the arrangement is suitably damped mechanically (the degree of which can be determined by straightforward trials), this ratio can be varied over time and a y scan can be executed. Thus, a suitable waveform 200 is shown in FIG. 13. Waveform 200 is comparable to waveform 84 of FIG. 8C and with pulses also of amplitude A, but waveform 200 has three positive pulses followed by one negative pulse, each separated by the resting phase. On average, this waveform has a value of 0.5 A. If the waveform includes four positive pulses followed by a negative pulse, it would have an average value of 0.6 A. Thus, if waveform 200 has m positive pulses followed by n negative pulses, the fork is moved to (m−n)/(m+n) of its maximum y deflection, without employing an actual DC offset. As will be apparent, this may be a positive or negative deflection depending on the values of m and n. Consequently, by varying the number of positive and negative pulses in waveform 200, it is possible to obtain to within an acceptable the desired y deflection.

The waveforms of FIGS. 8A, 8B, 8C, 8D and 13 are synchronized waveforms with no pulse mutilation due to mid pulse reversal. Some reversals during mid pulse could be tolerated if done quickly enough and small glitches would be smoothed by mechanical Q. However, in order to obtain the highest image quality and frame to frame averaging, a synchronized system is preferable.

Modifications within the scope of the invention may be readily effected by those skilled in the art. It is to be understood, therefore, that this invention is not limited to the particular embodiments described by way of example hereinabove.

In the preceding description of the invention and the following claims, except where the context requires otherwise owing to express language or necessary implication, the word "comprise" or variations such as "comprises" or "comprising" is used in an inclusive sense, i.e. to specify the presence of the stated features but not to preclude the presence or addition of further features in various embodiments of the invention.

Further, any reference herein to prior art is not intended to imply that such prior art forms or formed a part of the common general knowledge.

The invention claimed is:

1. A scanning apparatus, comprising:
   a fork with first and second forwardly extending tines and a rearwardly extending counterweight member;
   a mount for supporting said fork at a point between said tines and said counterweight member; and
   a drive for effecting relative vibration between said tines to provide a fast scan and for driving said fork to provide a slow scan transverse to said fast scan.

2. A scanning apparatus as claimed in claim 1, wherein said fork is mounted substantially at its centre of mass.

3. A scanning apparatus as claimed in claim 1, wherein said drive comprises first and second electromagnetic drives, the first magnetic drive comprising an x-drive coil located about said tines and the second electromagnetic drive comprising a y-drive coil located about said counterweight member, wherein the x-drive coil and the y-drive coil are stationary relative to the mount.

4. A scanning apparatus as claimed in claim 3, wherein said drive further includes a magnet located on said first tine.

5. A scanning apparatus as claimed in claim 1, wherein said drive comprises an electromagnetic drive comprising a single drive coil located about said fork.

6. A scanning apparatus as claimed in claim 1, further comprising a stabilizing magnet located rearward of said counterweight member for defining an approximate location of said counterweight member when said apparatus is not in use and an approximate operational centre of said counterweight member when said apparatus is in use.

7. A scanning apparatus as claimed in claim 6, wherein said stabilizing magnet has a boss or protrusion facing said counterweight member for concentrating the magnetic field lines of said stabilizing magnet in the vicinity of said boss or protrusion.

8. A scanning apparatus as claimed in claim 1, wherein said mount comprises a deformable material with an aperture in which the fork is located, wherein the deformable material deforms to accommodate motion of the fork.

9. A scanning apparatus as claimed in claim 8, wherein said deformable material is a visco-elastic material.

10. A scanning apparatus as claimed in claim 8, wherein said deformable material is sorbothane brand polyurethane material.

11. A scanning apparatus as claimed in claim 1, further comprising a z-axis drive, for driving said fork forwardly and rearwardly.

12. A scanning apparatus as claimed in claim 11, wherein z-axis drive comprises a nitinol wire drive.

13. A scanning apparatus as claimed in claim 1, comprising an optical head of approximately 5 mm diameter and 45 mm length, exclusive of an optical head casing.

14. A scanning apparatus as claimed in claim 1, comprising an optical head of approximately 3.5 mm diameter and length of at least 100 mm, exclusive of an optical head casing.

15. A scanning apparatus as claimed in claim 1, comprising an optical head of approximately 4.4 mm diameter and lengths of greater than or approximately equal to 300 mm, inclusive of an optical head casing.

16. An optical head comprising a scanning apparatus as claimed in claim 1.

17. An optical instrument comprising a scanning apparatus as claimed in claim 1.

18. An optical instrument as claimed in claim 17, wherein said optical instrument is an endoscope, a microscope or an endomicroscope.

19. A scanning method comprising:
   supporting a fork having first and second forwardly extending tines and a rearwardly extending counterweight member at a point between said tines and said counterweight member;
   driving at least one of the first and second tines to vibrate relative to the other of the first and second to provide a fast scan; and moving said fork to provide a slow scan transverse to said fast scan.

20. A method as claimed in claim 19, including supporting said fork substantially at the centre of mass of said fork.

21. A method as claimed in claim 19, including driving at least one of said first and second tines by means of a first drive coil located about said tines and moving said fork to provide said slow scan by means of a second drive coil located about said counterweight member, wherein said x-drive coil and said y-drive coil are stationary relative to a point at which said fork is supported.

22. A method as claimed in claim 19, wherein said drive comprises an electromagnetic drive comprising a single drive coil located about said fork.

23. A method as claimed in claim 22, including driving said coil with a waveform comprising sequences of positive and negative pulses separated by resting phases, and controlling instantaneous y deflection by controlling the ratio of positive pulses to negative pulses.

* * * * *